United States Patent [19]

Wood

[11] 4,309,509

[45] Jan. 5, 1982

[54] ODORANT HYDROPHILIC FOAM COMPOSITIONS

[75] Inventor: Louis L. Wood, Rockville, Md.

[73] Assignee: W. R. Grace & Co., New York, N.Y.

[21] Appl. No.: 129,152

[22] Filed: Mar. 10, 1980

[51] Int. Cl.$^3$ .................... C08G 18/14; C08G 18/08; A61K 7/36

[52] U.S. Cl. .................... 521/132; 424/28; 424/78; 521/159; 521/905; 521/137

[58] Field of Search ............. 521/905, 159, 132, 137; 424/28, 78

[56] References Cited

U.S. PATENT DOCUMENTS

| | | | |
|---|---|---|---|
| 3,903,232 | 9/1975 | Wood et al. | 521/905 |
| 3,939,260 | 2/1976 | Lafon | 424/28 |
| 3,975,350 | 8/1976 | Hudgin et al. | 260/30.4 N |
| 4,137,200 | 1/1979 | Wood et al. | 521/159 |
| 4,226,944 | 10/1980 | Stone et al. | 521/905 |
| 4,271,272 | 6/1981 | Strickman et al. | 521/110 |

FOREIGN PATENT DOCUMENTS 1478000  6/1977  United Kingdom ............ 521/132

*Primary Examiner*—H. S. Cockeram
*Attorney, Agent, or Firm*—Richard P. Plunkett; William W. McDowell, Jr.

[57] ABSTRACT

This invention relates to hydrophilic, odorant-containing foam compositions having improved release ability of the odorant abetted by incorporating the odorant into a non-volatile, water insoluble oil or wax medium which is added to an aqueous reactant prior to reacting the aqueous reactant with a hydrophilic, isocyanate-terminated prepolymer to form a polyurethane foam.

5 Claims, No Drawings

ODORANT HYDROPHILIC FOAM COMPOSITIONS

FIELD OF THE INVENTION

This invention relates to new, hydrophilic, odorant-containing foam compositions having improved liberation of the odorant.

Numerous attempts have been made in the prior art seeking solutions to improve air freshening with odorants.

Sachets perfumed with various fragrances, e.g., lilac, were disposed in drawing rooms. These had the drawback of poor longevity. Containers filled with liquid scents from which a wick extended have been employed in households since 1944. However, the ability to spill and lack of aesthetic value deterred their commercial acceptance. Gels based on natural products such as polysaccharides and proteins such as carrageenates, alginates, pectins or gelatine have been used as perfume carriers. These materials, apart from not being available in sufficient quantities, have the drawbacks of high shrinkage and poor dimensional stability to heat. Air fresheners, per se, have also been added to foams. However, the foams release the fragrances too quickly to be of commercial value.

By the present invention, odorant-containing polyurethane foam is prepared by reacting a prepolymer comprising a particular isocyanate-capped polyoxyethylene polyol with large amounts of an aqueous reactant containing an odorant incorporated into a non-volatile, water insoluble oil or wax medium. The thus generated polyurethane foam having the odorant uniformly disposed throughout is found to liberate the odorant uniformly over an extended period of time in a controlled manner.

DESCRIPTION OF PRIOR ART

It is known from U.S. Pat. No. 4,137,200, incorporated herein by reference in its entirety, to make hydrophilic polyurethane foams by reacting an isocyanate-terminated prepolymer formed from a hydrophilic polyether polyol, e.g., polyoxyethylene polyol and a polyisocyanate, and with a water reactant.

It is also known from British Pat. No. 1,478,000 to use hydrophilic polyurethane gels as perfume carriers. These hydrophilic gel materials because of the quick release of the fragrance are receiving poor commercial acceptability.

OBJECT OF THE INVENTION

One object of the instant invention is to produce a hydrophilic, odorant-containing foam composition having improved release ability of the odorant. Another object of the instant invention is to produce a hydrophilic, odorant-containing foam composition having good release ability of the odorant wherein the foam can be either open cell or reticulated. Yet another object of the instant invention is to produce a hydrophilic, odorant-containing foam which will liberate the odorant uniformly over an extended period of time.

This and other objects, which will become apparent from a reading hereinafter, are obtained from a composition comprising (a) a water reactant; (b) a prepolymer comprising at least one isocyanate-capped polyol having a reaction functionality of at least two, the total of said polyol present having an oxyethylene content of at least 40 weight percent before capping; (c) when the reaction functionality of (b) is two, a crosslinking agent containing at least 3 functional groups; and (d) at least one odorant incorporated into a non-volatile, water insoluble oil or wax medium, the weight ratio of (a):(b) being 0.25 to 2.0:1.0.

Various combinations of (b), per se, or with (c) supra are operable to form the hydrophilic, isocyanate-terminated prepolymers operable in the present invention. One example to form (b) supra would be to cap a polyoxyethylene containing diol with a diisocyanate such that the capped product had a reaction functionality of 2. Since this material, per se, will not yield a crosslinked foam on addition of a water reactant, it is necessary to add thereto either (1) a diol capped with a polyisocyanate having a functionality greater than two, e.g., benzene-1,3,5-triisocyanate;

(2) a polyol containing at least 3 OH groups capped with a di- or polyisocyanate;

(3) an isocyanate-reactive crosslinking agent such as one having from 3 up to 6 or more reactive amine, hydroxy, thiol or carboxylate sites per average molecule which is added to the water reactant or (4) a combination of (1) and (2).

Other examples of (b) operable herein to form foams would be (1) or (2) supra, per se, or blended together with or without (3).

When two or more isocyanate-capped polyols are blended to form (b), the oxyethylene present in the polyol or blend of polyols can be present in only one polyol, some of the polyols or in each polyol as long as the amount is equal to at least 40 weight percent of the polyols present before capping with the di- or polyisocyanate.

The polyurethane foam used herein is made by the prepolymer method using a large excess of water in accord with the method set out in U.S. Pat. No. 4,137,200, incorporated in its entirety herein by reference.

The present crosslinked, hydrophilic odorant-containing foams may be prepared from a prepolymer formed by capping polyoxyethylene polyol with a polyisocyanate such that the capped prepolymer has a reaction functionality greater than two. The capped prepolymer is then formed into foam simply by being added to and reacting with an aqueous reactant containing the odorant incorporated in a non-volatile, water insoluble oil or wax medium. As used herein, the term "incorporated" when referring to the odorant in the oil or wax medium means that the odorant is dissolved or dispersed in the medium. Optionally, the capped product and/or aqueous reactant may contain a suitable crosslinking agent, if desired, in which case the capped polyoxyethylene polyol product may have a functionality approximating two.

During capping it is desirable that polyisocyanate be reacted with the polyol such that the reaction product, i.e., the capped product, is substantially void of reactive hydroxy groups while containing more than two reactive isocyanate sites per average molecule.

Another route for achieving this desired result is to react, during the foaming reaction, an isocyanate-capped diol having two reactive isocyanate sites per average molecule, in a reaction system containing a polyfunctional reactive component, such as one having from three up to six or more reactive amine, hydroxy, thiol or carboxylate sites per average molecule. These latter sites are highly reactive with the two reactive isocyanate sites.

Polyoxyethylene polyol used as a reactant in preparing the isocyanate-capped prepolymer may have a weight average molecular weight of about 200 to about 20,000, and preferably between about 600 to about 6,000, with a hydroxyl functionality of about two or greater, preferably from about 2 to about 8.

Polyoxyethylene polyol is terminated or capped by reaction with a polyisocyanate. The reaction is preferably carried out in an inert moisture-free atmosphere such as under a nitrogen blanket, at atmospheric pressure at a temperature in the range of from about 0° C. to about 120° C. for a period of time of up to about 80 hours depending upon the temperature and degree of agitation. This reaction may be effected also under atmospheric conditions provided the product is not exposed to excess moisture. The polyisocyanates used for capping the polyoxyethylene polyol include PAPI (a polyaryl polymethylene-polyisocyanate as defined in United States Patent No. 2,683,730), tolylene diisocyanate, triphenylmethane-4,4',4''-triisocyanate, benzene-1,3,5-triisocyanate, toluene-2,4,6-triisocyanate, diphenyl-2,4,4'-triisocyanate, hexamethylene diisocyanate, xylene diisocyanate, chlorophenylene diisocyanate, diphenylmethane-4,4'-diisocyanate, naphthalene-1,5-diisocyanate, xylene-alpha, 3,3'-dimethyl-4,4'-biphenylene diisocyanate, 3,3'-dimethoxy-4,4'-biphenylene diisocyanate, 2,2',5,5'-tetramethyl-4,4'-biphenylene diisocyanate, 4,4'-methylene bis(phenylisocyanate), 4,4'-sulfonyl bis(phenyl-isocyanate), 4,4'-methylene di-orthotolylisocyanate, ethylene diisocyanate, trimethylene diisocyanate, diicyclohexyl methane-4,4'-diisocyanate, isophorone diisocyanate, 1,6-hexa-methylene diisocyanate, 2,2,4-trimethyl-1,6-hexane diisocyanate and the like. Mixtures of any one or more of the above mentioned organic isocyanates may be used as desired. The aromatic diisocyanates, aliphatic and cycloaliphatic diisocyanates and polyisocyanates or mixtures thereof which are especially suitable are those which are readily commercially available, have a high degree of reactivity and a relatively low cost.

Capping of the polyoxyethylene polyol may be effected using stoichiometric amounts of reactants. Desirably, however, an excess of polyisocyanate is used to insure complete capping of the polyol. Thus, the ratio of isocyanate groups to the hydroxyl groups used for capping is between about 1 to about 4 isocyanates per hydroxyl, preferably 1.8 to 3.0 isocyanate groups per hydroxyl.

Isocyanate-capped polyoxyethylene polyol reaction products (prepolymers) employed in the present invention may be exemplified as follows. First, when water is the sole reactant with the isocyanate groups of the prepolymer during the foaming process, the isocyanate-capped polyoxyethylene polyol reaction product must have an average isocyanate functionality greater than two and up to about eight or more depending upon the composition of the polyol and capping agent components. Secondly, when the isocyanate-capped polyoxyethylene polyol has an isocyanate functionality of only about two, then the water or aqueous reactant used may contain a dissolved or dispersed isocyanate-reactive crosslinking agent having an effective functionality greater than two. In this latter case, the reactive crosslinking agent is reacted with the capped polyoxyethylene polyol during the foaming process.

Conventional water soluble or water dispersible isocyanate-reactive crosslinking agents having an active functionality greater than two include those containing amine, thiol and carboxylate groups. Examples of such crosslinking agents include, but are not limited to, ethylene diamine, diethylene triamine, n-methyl ethylene diamine, cyclopentane-tetracarboxylic acid, 1,3,5-benzene tricarboxylic acid, citric acid, trimethylolpropane tris($\beta$-mercaptopropionate) and pentaerythritol tetrakis($\beta$-mercaptopropionate), triethylenetetramine, tetra-ethylenepentamine, polyethyleneimine, tolylene-2,4,6-triamine, trimethylenediamine, tetramethylenediamine, pentamethylenediamine, hexamethylene-diamine, ethanolamine, diethanolamine, hydrzine, triethanolamine, benzene-1,2,4-tricarboxylic acid, nitrilotriacetic acid and 4,4'-methylenebis(o-chloroaniline).

Thirdly, when the isocyanate-capped polyoxyethylene polyol has an isocyanate functionality of only about two, then a polyisocyanate crosslinking agent having an isocyanate functionality greater than two may be incorporated therein, either preformed or formed in situ, and the resultant mixture is reacted with water or aqueous reactant containing the odorant incorporated in a non-volatile, water insoluble oil or wax medium and optionally containing a dissolved or dispersed reactive isocyanate-reactive crosslinking agent, leading to a crosslinked, hydrophilic, odorant-containing polyurethane foam.

Several different modes may be used to prepare the prepolymer, i.e., the hydrophilic capped polyoxyethylene polyol reaction product having an average isocyanate functionality greater than two. In forming the prepolymer, blends or mixtures of the various polyols and/or polyisocyanates may be used as desired so long as the total average isocyanate functionality of the final urethane containing reaction product is greater than two and the ethylene oxide content of the polyol is at least 40 weight percent prior to capping.

One useful mode is to polymerize ethylene oxide in the presence of a polyfunctional hydroxyl containing starter component, such as glycerol, trimethylolpropane or trimethylolethane, which leads to polyoxyethylene triols. The molecular weight of these polymeric triols may be varied greatly, depending on the number of moles of ethylene oxide used in the reaction with the starter component. Starter components such as pentaerythritol and sucrose likewise treated with ethylene oxide lead to polymeric polyoxyethylene tetrols and hexols, respectively. Alternatively, polyols suitable for capping with polyisocyanate may be prepared from diols, triols, tetrols, hexols and polycarboxylic acids.

A second possible method for preparing the prepolymer is by reacting polyoxyethylene glycol having a reactive functionality equal to two with a molar excess of a diisocyanate which leads to an isocyanate-capped polyurethane product (A) having an isocyanate functionality of two. A polyol such as pentaerythritol having a reactive functionality equal to four is reacted with a large molar excess of a diisocyanate to form an isocyanate-capped polyurethane intermediate product (B) having an isocyanate functionality of four. By blending the two isocyanate-capped products thus prepared, i.e., products (A) and (B), in various molar proportions, the resulting product mixture has an average isocyanate functionality greater than two and on admixture with aqueous reactants containing the odorant in a wax medium will lead to the hydrophilic, crosslinked, polyurethane, odorant-containing foams of the present invention. In addition, other monomeric or polymeric polyisocyanate crosslinking agents may be substituted for the tetraisocyanate product (B). Tolylene-2,4,6-triisocyanate having a reactive functionality of three is an example of a simple monomeric triisocyanate which may be usefully employed to achieve the same objective of imparting to the system an average isocyanate functionality greater than two.

A third method for preparing the prepolymer is to blend a generally linear diol or polyol with a polyol having at least 3 and preferably from 3 to 8 hydroxyl groups (e.g., trimethylol-propane, trimethylolethane, glycerol, pentaerythritol or sucrose). Generally, monomeric polyols having 3 or 4 hydroxyl groups per mole are employed. The blend is then reacted with a sufficient amount of a polyisocyanate so that the resulting prepolymer is substantially void of unreacted hydroxyl groups, i.e., an excess of the polyisocyanate is preferably employed. The excess of polyisocyanate can range up to the point where about 4 isocyanate groups are employed for each hydroxyl group.

A fourth method would be to blend any combination of the prepolymer described in the first method with the constituents described in the second or third method either individually or collectively.

It has also been found that the capped polyoxyethylene polyol having an isocyanate functionality greater than two used to prepare a three-dimensional network polymer must be present in an amount sufficient to insure formation of the three-dimensional network. Thus, amounts of the capped polyoxyethylene polyol having an isocyanate functionality greater than two in the component to be formed into foam ranging from about 3% by weight of this component up to 100% by weight. Hence, it is possible to include an isocyanate capped diol having an isocyanate functionality of two, e.g., polyethylene gycol capped with toluene diisocyanate in an amount from 0% by weight up to about 97% by weight of the component to be formed into foam. The maximum amounts of diisocyanate used are limited to that necessary to permit crosslinking to take place during the particle forming reaction, as contrasted to formation of a linear polymeric structure.

The polyoxyethylene polyols used to form prepolymer in this invention are water-soluble reaction products derived from the polymerization of ethylene oxide in the presence of a polyfunctional starter compound such as water, ethylene glycol, glycerol, pentaerythritol, sucrose, and the like. The molecular weights may be varied over a wide range by adjusting the relative ratios of ethylene oxide monomer to starter compound. The operable molecular weight ranges have been described previously.

It is possible and sometimes desirable to incorporate various amounts of a relatively hydrophobic comonomer into the ethylene oxide based polymerization products used to form the hydrophilic prepolymer. Thus, comonomers such as propylene oxide or butylene oxide may be copolymerized as a random copolymer, block-copolymer or both, such that the copolymers remain hydrophilic while having other desirable features for certain applications, namely, improved low temperature flexibility and hydrolytic stability. Up to about 40-60 weight percent, but desirably about 25-45 weight percent of the relatively hydrophobic comonomer, may be copolymerized with the ethylene oxide monomer and still yield hydrophilic crosslinked solid polyurethane foams when those products are used as polyol intermediates in practicing the present invention. Thus, throughout the text of this document, the term "polyoxyethylene polyol" is intended to include not only homopolymers of ethylene oxide but also hydrophilic copolymers of ethylene oxide such as those described above wherein all of these polyol derivatives have a hydroxyl functionality of about two or greater and an oxyethylene content ranging from about 40 weight percent to about 100 weight percent and preferably greater than about 55 weight percent.

The molecular weights of the polyols herein are determined by calculation from the hydroxyl numbers and are number average molecular weights.

To effect foam formation with a crosslinked network, the prepolymer is simply added to and reacted with a particular aqueous component containing the odorant in a wax medium. For simplicity, this isocyanate-capped prepolymer will occasionally be referred to herein as "resin reactant".

The aqueous component prior to addition of the odorant-containing oil or wax may be water, a water slurry or suspension, a water emulsion or a water solution having water soluble materials disposed therein. For convenience, the aqueous component is referred to herein as an aqueous reactant.

In contrast to typical polyurethane reactions such as those using catalyst or like promoters where one mole of —NCO is reacted with one half mole water, the present reaction proceeds simply with large excesses of water.

Because large amounts of water are in the aqueous reactant during reaction, i.e., the present invention is not dependent upon a stoichiometric molar NCO-water type reaction, it is possible to combine a great variety of materials in the aqueous reactant which are otherwise not possible with limited water reacting systems.

The aqueous reactant may be used to incorporate the odorant and to form foam at temperatures from slightly above 0° C. up to about 60° C., preferably from slightly above 0° C. up to 40° C., in order to minimize loss of the volatile odorant. This temperature can be readily determined and can be modified by the use of catalysts in the aqueous phase.

In typical polyurethane reactions known to the art, it is known to employ an excess of water in prepolymer foaming formulations to obtain improved properties. It is further known that, if less than stoichiometric amounts of water are used, the foam is more crosslinked, firmer, has lower elongation and higher density. It is commonly taught in the prior art that a large excess of water will use up the free isocyanate groups, leaving insufficient isocyanate available for effective crosslinking and resulting in the formation of many free amino end groups. As water content increases, the foam density decreases and above 30–50% excess water over stoichiometry results in a marked decrease in physical properties.

The dramatic way in which the addition of water influences practice of the present invention is seen by consideration of the Water Index Value defined as equivalents of $H_2O \times 100$ divided by equivalents of NCO. In polyurethane foaming reactions one mole of water ultimately consumes 2 NCO groups, i.e., 1.0 mole $H_2O = 2$ equivalents —OH which react with 2 equivalents of NCO. A Water Index Value of 100 indicates the equivalents of water and equivalents of isocyanate are balanced. An Index of 95 indicates that there is a 5% shortage of water equivalents while an Index of 105 indicates a 5% surplus of water equivalents. A slight shortage of water equivalents (i.e., a slight excess of isocyanate), usually 3–5%, is common practice in the prior art, particularly with flexible foams.

Using the present resin reactant and water in amounts from about 0.5 mole $H_2O$/mole NCO groups ($H_2O$ Index Value of 100) up to about 2 moles $H_2O$/mole NCO groups ($H_2O$ Index Value of 400) results in poor foaming unless materials such as surfactants and catalysts or the like are included. Amounts up to about 2 moles $H_2O$/mole NCO ($H_2O$ Index Value of 400) require a catalyst. When using about 6.5 moles $H_2O$ mole/NCO groups ($H_2O$ Index Value of 1,300) up to about 390 moles $H_2O$/mole NCO groups, ($H_2O$ Index Value 78,000), surprisingly good foams result which improve in characteristics with added amounts of molar water. Thus, the available water content in the aqueous reactant is from about 6.5 to about 390 moles $H_2O$/NCO groups in the resin reactant, i.e., an $H_2O$ Index Value of about 1,300 to about 78,000 and desirably from about 4,000 to about 40,000, i.e., about 20 to about 200 moles $H_2O$/NCO groups.

"Available water" in the aqueous reactant is that water accessible for reaction with the resin reactant and which is exclusive of water which may layer during reaction or supplemental water which may be necessary because of further water-absorbtive or water-binding components or additives present in and forming the aqueous reactant.

The use of large molar excesses of water in the aqueous reactant leads to several important advantages and improvements over the conventional polyurethane foam compositions. For example, in conventional one shot polyurethane foam compositions, the water concentration must be carefully controlled to near the theoretical amount, usually an amount much less than about an $H_2O$ Index Value of 400 (2.0 moles $H_2O$/NCO groups in the polyurethane reaction components) and the odorant is usually included separately thereafter. This low concentration dictates the use of a catalyst to promote the rate of the polymerization foaming reaction and requires an intensive mixing step to achieve good mixing of reactants and catalyst so as to insure a controllable and uniform cellular product, other additives are avoided. In contrast, the present polyurethane foam requires very large but controlled excess of water, e.g., typically about an $H_2O$ Index Value of about 1,300 to about 78,000. Using this technique, the product quality and uniformity is not highly sensitive to accuracy of metering or mixing of the aqueous reactant and the use of a polymerization catalyst or promoter is optional. Thus, the odorant in the oil or wax medium is included in the polyurethane structure at the time of foaming.

The hydrophilic foams of the present invention may be formulated so as to be flexible, semi-rigid or rigid in nature and to be of primarily open cell or reticulated structure as desired.

The term "odorant" as used herein includes all the volatile aromatic individual components or compositions known under the headings of volatile ethereal oils, perfumes, fragrances, essences or scents and additionally synthetic odorants and fragrances. It is immaterial to the process according to the present invention whether the odorant substances are soluble in the dispersing agent or may only be emulsified or dispersed therein as long as they volatilize at a controlled rate from the non-volatile, water-insoluble oil or wax medium in the foam at atmospheric or superatmospheric conditions of temperature, i.e., at a temperature of 14° C. and above.

The following are examples of etherical oils: aniseed oil, oil of bergamot, camphor oil, citronella oil, lemon oil, eucalyptus oil, the various pine needle oils, geranium oil, oil of lavender, lemon grass oil, clove oil, oil of orange, peppermint oil, attar of roses, spike lavender oil, oil of turpentine and oil of cinnamon. These are complex mixtures of alcohols, aldehydes, ketones, esters, oxides, lactones, terpenes and many other, in some cases as yet unidentified compounds.

The term "scents" is used here to denote chemically exactly defined individual substances which may either be isolated from ethereal oils or produced synthetically, for example, anethole, anisaldehyde, vanillin and citronellal. By "perfumes" are meant aromatic mixtures in a solvent, and these mixtures may be composed of ethereal oils and scents. Odorants can be used individually or admixtures of various odorants can be employed.

The medium for the odorant can not only be a solid or semi-solid wax at ambient conditions but also an oil. Such oils function in the same manner as the solid waxes in slowing down the migration of the odorants from the foam composition into the environment. To function optimumly in the hydrophilic foam system, the oils like the waxes should be hydrophobic and relatively non-volatile so that they husband the odorants in separate, relatively self-contained and long lasting microcellular regions suspended in the hydrophilic foam matrix.

The non-volatile, water insoluble waxes used as a medium in which the odorant can be incorporated herein are those having a melting point in the range 30°–100° C. and can be selected from various classes of waxes including plant, animal (including insect), mineral (including petroleum) and synthetics. Operable species of natural waxes include beeswax, bayberry-myrtle, candelilla, caranday, carnauba, castor bean wax, esparto grass wax, Japan wax, montan crude wax, ouricury, retamo-cerinimbi, shellac wax, spermaceti, sugar cane wax and wool wax-lanolin. Mineral waxes include peat wax, montan wax, ozocerite and paraffin waxes. Synthetic waxes include Hoechst Wax S, Hoechst Wax L, Hoechst Wax E, Hoechst Wax OP, polyethylene wax, oxidized polyethylene wax, polypropylene wax, chlorinated paraffins and oxidized hydrocarbon wax products such as those from the Fisher-Tropsch paraffins and the microcrystalline petroleum waxes.

The odorant in the wax medium is usually formed by melting the wax, admixing the odorant in the melt and thereafter adding the molten admixture to the aqueous reactant with high agitation so as to form small droplets or particles therein. The molten odorant wax mixture can be jet-sprayed into the aqueous reactant to insure the formation of small particles. The aqueous reactant containing the odorant in the wax medium in the form of particles is then reacted with the hydrophilic prepolymer to form the foam.

Another method which could be used is to add the odorant to a molten wax medium and allow the admixture to solidify. The thus formed solid could then be grounded to particles which can be added to the aqueous reactant prior to its use in the foaming step with the hydrophilic prepolymer.

The non-volatile, water insoluble oils used as a medium for the odorant in this invention are those having a boiling point greater than 175° C. The oils can be selected from various classes in the oils including vegetable, petroleum, mineral and synthetic oils.

The odorant in the oil medium is usually formed by dissolving the odorant in the oil at about room temperature with good stirring and thereafter adding the solution to the aqueous reactant with high agitation to form a stable emulsion of the oil and odorant in water. The aqueous reactant containing the emulsion of oil and odorant is then reacted with the hydrophilic prepolymer to form the foam.

The operable and preferred weight ranges of the components required to make the odorant-containing foam of the instant invention are as follows:

| Component | Operable Range Parts by Weight | Preferred Range Parts by Weight |
|---|---|---|
| Hydrophilic isocyanate terminated prepolymer | 100 | 100 |
| Water reactant | 25–200 | 75–150 |
| Non-volatile H$_2$O insoluble wax or oil | 5–100 | 10–50 |
| Odorant | 1–30 | 3–15 |

In addition to the above required components it is also possible, if desired, to add up to 5 parts per 100 parts of prepolymer of a surfactant, 0.1 to 5 parts of a colorant per 100 parts of prepolymer and up to 10 parts per 100 parts of prepolymer of a blowing agent. Should the addition of an isocyanate-reactive, crosslinking agent be necessary to form a crosslinked foam, it would be added in an amount in the range 5 to 100 parts depending on the equivalent weight of the crosslinking agent.

The following examples are set out to describe, but expressly not limit, the instant invention. Unless otherwise noted, all parts of percentages are by weight.

PREPARATION OF PREPOLYMER

EXAMPLE 1

A prepolymer was prepared by admixing 2 molar equivalents of polyethylene glycol having an average molecular weight of 1,000 (PEG-1,000) and 0.66 molar equivalent of trimethylolpropane (TMOP). The admixture was dried at 100°–110° C. under a pressure of 5–15 Torr to remove water. The resulting dried mixture was slowly added over a period of about one hour to a vessel containing 5.50 molar equivalents of toluene diisocyanate (TDI) while stirring the TDI and polyol mixture. The temperature was maintained at 60° C. The mixture was maintained at 60° C. with stirring for three additional hours. The amount of TDI employed was about 92% of that theoretically required to cap all hydroxyl groups in the polyol mixture using only one isocyanate group on the diisocyanate. However all hydroxyl groups were capped with isocyanate due to chain-extension occurring between the polyols and TDI. The prepolymer will hereinafter be referred to as Prepolymer A.

PREPARATION OF ODORANT-CONTAINING FOAM

EXAMPLE 2

To a 40 g portion of paraffin wax (m. p. 60°–62° C.) at 70° C. was added with good stirring 12 g of a concentrated lemon fragrance. The resultant solution, while still molten, was poured into 200 g of water containing 2 g of a nonionic surfactant having an average molecular weight of 4150 sold under the tradename "PLURONIC P-75" by BASF, Wyandotte, which was being stirred at high shear in a Waring blender at 25° C. 30 seconds after the addition was complete, there was formed a stable emulsion suspension of a odorant-containing solid wax in water.

80 g of Prepolymer A from Example 1 was added to 101 g of the emulsion suspension prepared above. The admixture was agitated for about 15 seconds using an electric drill fitted with a paint mixer disk at 25° C. After about 6 minutes foaming was complete. The resultant foam contained uniform open cells and had a wet density of 7.1 lbs/ft$^3$.

A control foam was prepared in the same manner without the paraffin wax by adding 80 g of Prepolymer A from Example 1 to 80 g of water containing 0.8 g of "PLURONIC P-75" and 4.8 g of concentrated lemon fragrance. The resultant foam had a uniform open cell structure and a wet density of 6.8 lbs/ft$^3$.

From each of the above wet foams was cut a 2"×4"×½" sample. Each foam sample on a 4" glass dish was placed in a circulating air oven at 50° C. and 10 Torr for 48 hours. After vacuum oven treatment each foam sample was then placed by itself in a 16 ounce wide mouth jar with tight lid for 16 hours at 25° C. The caps were then removed from the jars and the contents smelled immediately. The fragrance smell was much stronger in the jar containing the foam wherein the odorant was in a waxed medium. This is evidence that the foam-containing odorant in a wax medium retains the fragrance over a longer time period than that wherein the odorant, per se, is present in the foam.

The odorant-containing foams have many uses including underarm shields, air fresheners for rooms and refrigerators and the like.

EXAMPLE 3

To a 40 g portion of paraffin oil (Saybolt viscosity 345 sec. at 100° F.) at 25° C. was added with good stirring 12 g of a concentrated lemon fragrance. The resultant solution was poured into 200 g of water containing 2 g of a nonionic surfactant having an average molecular weight of 4150 sold under the tradename "PLURONIC P-75" by BASF, Wyandotte, which was being stirred at high shear in a Waring blender at 25° C. 30 seconds after the addition was complete, there was formed a stable emulsion of oil and fragrance in water.

80 g of Prepolymer A from Example 1 was added to 101 g of the emulsion prepared above. The admixture was agitated for about 15 seconds using an electric drill fitted with a paint mixer disk at 25° C. After about 6 minutes foaming was complete. The resultant foam contained reticulated cells and had a wet density of 7.3 lbs/ft$^3$.

A control foam was prepared in the same manner without the paraffin oil by adding 80 g of Prepolymer A from Example 1 to 80 g of water containing 0.8 g of "PLURONIC P-75" and 4.8 g of concentrated lemon fragrance. The resultant foam had a reticulated cell structure and a wet density of 7.2 lbs/ft$^3$.

From each of the above wet foams was cut a 2"×4"×½" sample. Each foam sample on a 4" glass dish was placed in a circulating air oven at 50° C. and 10 Torr for 48 hours. After vacuum oven treatment each foam sample was then placed by itself in a 16 ounce wide mouth jar with tight lid for 16 hours at 25° C. The caps were then removed from the jars and the contents smelled immediately. The fragrance smell was much stronger in the jar containing the foam wherein the odorant was in an oil medium. This is evidence that the foam-containing odorant in an oil medium retains the fragrance over a longer time period than that wherein the odorant, per se, is present in the foam.

The odorant-containing foams have many uses including underarm shields, air fresheners for rooms and refrigerators and the like.

I claim:

1. An odorant-containing, urethane foam forming composition comprising
   (a) 25–200 parts of a water reactant;
   (b) 100 parts of a prepolymer comprising at least one isocyanate-capped polyol having a reaction functionality greater than two, the total of said polyol present having an oxyethylene content of at least 40 weight percent before capping;
   (c) 5–100 parts of a non-volatile, water insoluble wax or oil said wax or oil having incorporated therein
   (d) 1–30 parts of a volatile odorant.

2. The composition of claim 1 containing in addition up to 5 parts of a surfactant.

3. The composition of claim 1 wherein the odorant-containing medium is a wax.

4. The composition of claim 1 wherein the odorant-containing medium is an oil.

5. A hydrophilic polyurethane foam containing a volatile odorant incorporated in a non-volatile, water insoluble wax or oil formed by reacting 100 parts of a prepolymer comprising at least one isocyanate-capped polyol having a reaction functionality greater than two, the total of said polyol present having an oxyethylene content of at least 40 weight percent before capping, with 25 to 200 parts of a water reactant containing 1 to 30 parts of a volatile odorant incorporated in 5 to 100 parts of a non-volatile, water insoluble wax or oil.

* * * * *